United States Patent [19]

Kishida et al.

[11] 4,097,353

[45] Jun. 27, 1978

[54] ARTICLE AND METHOD OF FORMING POROUS COATING ON ELECTRODE LAYER OF CONCENTRATION CELL TYPE OXYGEN SENSOR

[75] Inventors: Katsuhiro Kishida, Yokohama; Hiroshi Takao, Kamakura; Kimmochi Togawa; Kazuo Matoba, both of Yokohama, all of Japan

[73] Assignee: Nissan Motor Company, Limited, Yokohama, Japan

[21] Appl. No.: 694,698

[22] Filed: Jun. 10, 1976

[30] Foreign Application Priority Data

Jun. 10, 1975 Japan ................................. 50-69173

[51] Int. Cl.² ............................................. G01N 27/26
[52] U.S. Cl. ................................ 204/195 S; 427/34; 427/402; 427/243
[58] Field of Search ................... 427/34, 57, 203, 204, 427/205, 243, 247, 294, 402, 421, 422, 423, 430; 204/195 S

[56] References Cited

U.S. PATENT DOCUMENTS

| | | | |
|---|---|---|---|
| 3,335,025 | 8/1967 | Rightmire et al. | 427/34 |
| 3,671,302 | 6/1972 | Nell et al. | 427/57 |
| 3,978,006 | 8/1976 | Topp et al. | 204/195 S X |

*Primary Examiner*—Harry J. Gwinnell
*Assistant Examiner*—S. Silverberg
*Attorney, Agent, or Firm*—Fleit & Jacobson

[57] ABSTRACT

A porous coating, which is effective in restricting the flow of a gas under measurement relatively to the electrode layer of the sensor and protecting the electrode against detrimental influences, is formed by spraying fine particles of a heat-resistant and chemically stable material at a high temperature onto the electrode surface to form a porous layer with pores of a moderate size, then impregnating the porous layer with an aqueous dispersion of fine particles of a similar material followed by baking the impregnated layer, so that the finished coating has pores of appropriate size and total volume.

9 Claims, 4 Drawing Figures

ARTICLE AND METHOD OF FORMING POROUS COATING ON ELECTRODE LAYER OF CONCENTRATION CELL TYPE OXYGEN SENSOR

This invention relates to a method of producing an oxygen sensing device for detecting oxygen concentration in a gas mixture. The device is of the concentration cell type having an ion conducting solid electrolyte layer, two electrode layers respectively formed on both sides of the electrolyte layer and a protective coating formed on one of the electrode layers which is to be exposed to the gas mixture. This invention relates particularly to a method of forming the protective coating.

In an internal combustion engine, the air to fuel ratio of an air-fuel mixture consumed in the combustion chambers of the engine significantly affects both the efficiencies of the engine and the composition of the exhaust gas. Ordinary gasoline engines, for example, work at best efficiencies when the air/fuel ratio approximates the stoichiometric ratio, i.e. 14.7-14.8 by weight. The employment of the stoichiometric air/fuel ratio is advantageous also to the function of a so-called three-way catalyst which can promote not only the oxidation of carbon monoxide CO and hydrocarbons HC but also the reduction of oxides of nitrogen NOx in the exhaust gas of the engine. The deviation of the air/fuel mixture from the stoichiometric ratio is commonly indicated by the term excess air factor $\lambda$, which is the ratio of the amount of air in the combustible mixture to that in the stoichiometric mixture of the same components. Accordingly, the value of $\lambda$ is larger than 1.0 for a lean mixture and smaller than 1.0 for a rich mixture.

Some of recent internal combustion engines are provided with a feedback control system for controlling the air/fuel ratio of a combustible mixture fed to the engine based on a certain characteristic of the exhaust gas. In such a control system, the concentration of oxygen in the exhaust gas is usually taken as the indication of an actual air/fuel ratio of the combustible mixture and is detected with an oxygen sensor.

A typical oxygen sensor now in practical use is fundamentally an oxygen concentration cell which consists essentially of a layer of a solid electrolyte whose conductivity is predominantly attributable to the migration of oxygen ions and two electrode layers formed respectively on the front and rear surfaces of the electrolyte layer. When a gas mixture such as an engine exhaust gas is present on one side of the cell and a reference gas such as air is present on the other side, the electromotive force of the cell depends on the ratio of the oxygen partial pressure of the reference gas to that of the gas mixture. The solid electrolyte is essentially an oxide of a tetravalent metal typified by zirconia $ZrO_2$ but is usually in the form of a solid solution of such a metal oxide and a stabilizing oxide exemplified by calcia CaO. The electrode layers are formed so porous as to be permeable to gas and in most cases are made of platinum.

In conventional oxygen sensors of the described type, particularly those which are for use in a heated gas mixture such as an exhaust gas containing various oxides and oxidizable substances in addition to oxygen, a stable and porous coating is frequently formed on the outside of one electrode layer in order to promote equilibrium reactions between oxygen and oxidizable substances such as CO and HC on the surface of the electrode layer and protect the electrode layer against detrimental physical and chemical influences. Such a coating is made from materials which are heat-resistant and chemically stable materials such as, for example, $Al_2O_3$, BeO, $ZrO_2$ and/or NiO. Sometimes, these materials are admixed with other materials such as, for example, Pt, Pd, Ru, Ir and/or Os which have a catalytic property on the aforementioned equilibrium reactions. Since the coating must be porous, these materials are used in the form of fine particles. Conventional methods of forming the porous coating on the electrode layer are divided roughly into the following two categories. The methods in the first category reside in spraying the fine particles at a high temperature against the outside of the electrode layer by, for example, plasma spraying or flame spraying. In the methods in the second category, the fine particles are dispersed in a liquid such as water, alumina sol, silica sol or water glass, and the dispersion is applied onto the surface of the electrode layer by brushing, vacuum impregnation, ultrasonic wave impregnation, immersion, spraying or an electrophoresis technique. Sometimes, alumina sol, silica sol or water glass alone is used as the material of the coating.

The advantages of the methods in the first category are ease in controlling the thickness of the coating, intimate and strong contact of the coating with the electrode layer and a relatively short response time of the sensor due to the presence of relatively large-sized pores in the coating. However, the pores are too large in size to allow a gas mixture to remain in contact with the electrode layer for a sufficiently long time, so that the sensor cannot provide a high output voltage. A coating formed by a method in the second category has the advantage that the pore size is small enough to allow the mixed gas to remain in contact with the electrode layer for a sufficiently long time. However, the contact of this coating with the electrode layer is unsatisfactory both in intimateness and bonding strength. Besides, the extremely small pore size constitutes an obstacle to diffusion of the mixed gas in the coating, resulting in poor responsiveness of the sensor.

With respect to an oxygen sensing device of the described type, it is an object of the invention to provide an improved method of forming a porous protective coating on an electrode layer of the oxygen sensing device, which method features ease in controlling the coating thickness, excellence in the contact of the coating with the electrode layer and appropriateness of the total pore volume and pore size distribution in the coating for the response time of the sensing device and contact of a gas mixture under measurement with the electrode layer.

The invention relates to an oxygen sensor having a layer of a solid oxygen-ion electrolyte provided with an electrode layer on each side thereof. According to the invention, a method of forming a porous coating on an electrode layer of the oxygen sensor comprises the following steps: (a) applying fine particles of a heat-resistant and chemically stable first material onto the surface of the electrode layer to form a porous layer by spraying the fine particles at a high temperature; (b) applying a dispersion of fine particles of a heat-resistant and chemically stable second material in a liquid onto the porous layer to impregnate the porous layer with the dispersion; and (c) baking the impregnated porous layer to fix the particles of the second material to the porous coating.

Typical examples of the first material are alumina and spinel, and the dispersion preferably contains alumina and/or silica. The first step is preferably carried out by plasma spraying using particles of 5 to 50 μm, and the second step is preferably carried out by vacuum impregnation.

The invention will fully be understood from the following detailed description with reference to the accompanying drawings, wherein.

Figure 3:
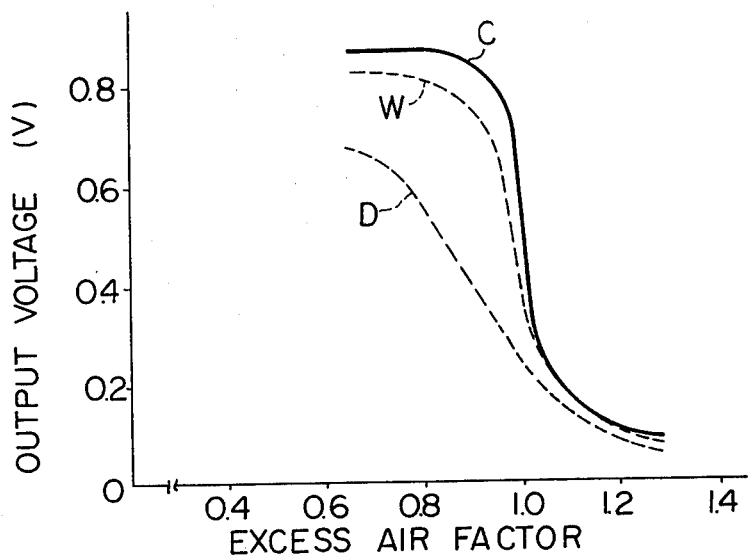
Figure 4:
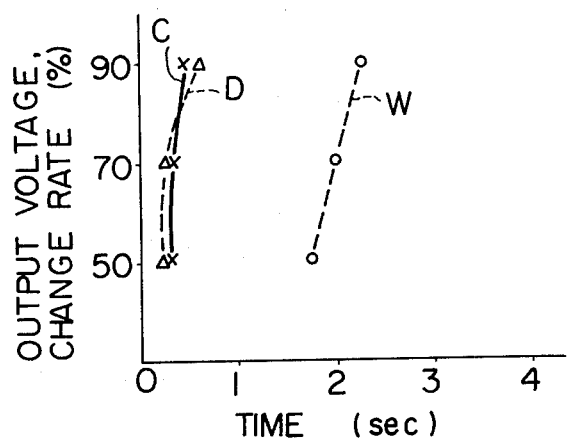

FIG. 3 is a graph showing the relationship between the excess air factor of a combustible mixture and the output voltage of an oxygen sensor which is provided with a porous coating on the electrode layer and exposed to the exhaust gas and the dependence of the output characteristics on the method of forming the coating; and FIG. 4 is a graph showing the variations in the responsiveness of the oxygen sensor depending on the method of forming the porous coating.

Figure 1:
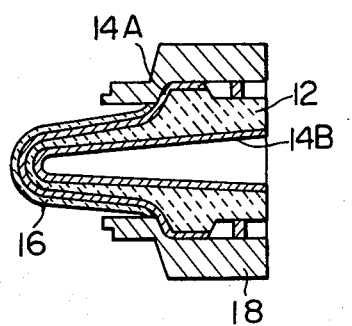
FIG. 1 is a sectional view of an oxygen sensor having a porous protective coating.

FIG. 1 shows an example of oxygen sensors as the object of the invention. This oxygen sensor has a layer of an ion-conducting solid electrolyte 12, which is so shaped (tubular in this example) that only one side (outside in this example) can be exposed to a gas mixture subject to measurement while the other side can be exposed only to a reference gas such as air. Two porous electrode layers 14A and 14B are formed on the outside and inside of the electrolyte layer 12, respectively. The outside of the outer electrode layer 14A is entirely coated with another porous layer 16 which is particularly concerned with in this invention. The reference numeral 18 indicates a metal bushing for fixing the sensor to a gas conduit such as an exhaust manifold of an engine.

As mentioned hereinbefore, the prous coating 16 serves both as a protector and as a diffuser. Main functions of the porous coating are; (1) to control the contact time of a gas mixture, for example an exhaust gas, under measurement with the electrode layer 14A thereby to promote equilibrium reactions between oxidizable substances such as CO and HC and oxygen on the surface of the electrode 14A, (2) to minimize the lowering in the surface temperature of the electrode layer 14A attributable to the variation in the flow rate of the gas mixture along the electrode layer 14A, and (3) to prevent deterioration of the electrode layer 14A and detachment of the electrode 14A from the solid electrolyte 12 by chemical and/or thermal influences. Accordingly the porous coating 16 must meet the following requirements; (a) to have pores which are appropriate both in their size and distribution for controlling the aforementioned contact time, (b) to have pores which are appropriate both in size and distribution for maintaining a good responsiveness of the sensor, (c) to be chemically stable and resistant to heat and thermal shocks resulting from rapid and frequent temperature changes, and (d) to remain in intimate and strong contact with the electrode layer 14A.

It is difficult to fully meet these requirements, particularly to simultaneously meet the requirement items (a) and (b) if the porous coating 16 is formed either by a dry process which consists of spraying fine particles of a chemically stable and heat-resistant material at a high temperature onto the surface of the electrode layer 14A or a wet process which consists of applying a dispersion of fine particles of a similar material in a liquid to the surface of the electrode layer 14A and baking the resulting coating on the electrode layer 14A. We have discovered that all of the above described requirements of the porous coating 16 can satisfactorily be met by the employment of a composite process in which the above defined dry process is initially carried out and then the wet process is carried out.

Preferred examples of materials useful for the dry process in a method according to the invention are alumina $Al_2O_3$, spinel (essentially $MgAl_2O_4$), alumina cement, beryllia BeO, zirconia $ZrO_2$, nickel oxide NiO, silicon carbide SiC, boron carbide $B_4C$ and boron nitride BN. Preferred materials useful for the subsequent wet process are silica sol, alumina sol, water glass and aqueous dispersion of γ-alumina. In addition, the above listed materials for the dry process are useful also for the wet process in the form of a dispersion in a liquid. Every material is used in the form of fine particles preferably within the particle size range from 5 to 50 μm. If the particle size is smaller than 5 μm, it is difficult to spray the particles at a high temperature, for example by plasma spraying. On the other hand, the pore size of the porous coating 16 becomes too large if the particle size of the material is larger than 50 μm.

Figure 2:
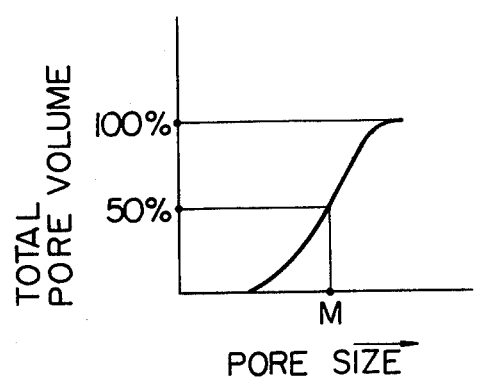
FIG. 2 is an explanatory cummulative pore volume curve with respect to the pore size in a porous coating.

We have examined variations in the total pore volume and pore size distribution in the porous coating 16 with variations in the method of forming the coating 16, and some experimental results are presented in Table 1. The mean pore size in Table 1 is represented by the pore size M in the cummulative pore volume (percentage) curve of FIG. 2 with respect to the pore size. The total pore volume reaches 50% on this curve at the pore size M.

Table 1

| Method | Material | Total pore volume $(cm^3/g)$* | Pore size range (μm) | Mean Pore size (μm) |
|---|---|---|---|---|
| Wet process (immersion) | alumina cement (dispersion in water) | 0.44 | 0.06–70 | 2.0 |
|  | alumina cement and water glass | 0.36 | 0.3–90 | 7.5 |
| Dry process (plasma spraying) | alumina cement | 0.13 | 0.15–80 | 40 |
|  | spinel | 0.49 | 0.10–90 | 30 |
|  | α-alumina | 0.16 | 0.10–90 | 30 |
| Composite process (Dry process followed by Wet process) | alumina cement (dry) and silica sol (wet) | 0.09 | 0.08–80 | 33 |
|  | spinel (dry) and silica sol (wet) | 0.16 | 0.009–85 | 23 |
|  | α-alumina (dry) and alumina sol (wet) | 0.09 | 0.09–85 | 15 |
|  | α-alumina (dry) and silica sol (wet) | 0.06 | 0.003–90 | 10 |
|  | α-alumina (dry) and aqueous dispersion of γ-alumina | 0.06 | 0.05–90 | 20 |

*pore volume per one gram of the porous coating.

As seen in Table 1, the total pore volume becomes smallest when the dry process is followed by the wet process in accordance with the invention. As to the pore size represented by the mean pore size corresponding to 50% cummulative pore volume, the composite process generally provides larger values than the wet process, but the dry process provides largest values.

When the oxygen sensor is used for estimating the air/fuel ratio of a combustible mixture consumed in an engine by measuring the oxygen concentration in the exhaust gas, it is desired that the exhaust gas attain an equilibrium state with respect to oxidation reactions of CO and HC at the three-phase boundary forming on the outside of the electrolyte layer 12. To attain the equilibrium state, the exhaust gas should come into contact with the electrode layer 14A at a moderate mass flow rate and remain there for a certain time. The permeation of the exhaust gas through the coating 16 is governed by the total pore volume of the coating 16, and the total pore volume is desired to be very small for effectively restricting the permeation or mass flow rate of the exhaust gas. The total pore volume per one gram of the coating 16 range of 0.09–0.16 cm$^3$/g realized by the composite process is considered quite appropriate to measure the exhaust gas in the equilibrium state.

The pore size of the coating 16 affects the response time of the oxygen sensor and of course is desired to be sufficiently large in this respect. However, the restriction to the mass flow rate of the exhaust gas through the coating 16 and maintenance of a sufficiently long contact time of the gas with the electrode 14A cannot be accomplished if the pore size is enlarged unlimitedly. The pore size range between 15 and 33 μm in Table 1 realized by the composite process is considered just appropriate.

The thickness of the coating 16 is controlled preferably within the range from about 5 to about 500 μm. Although the oxygen sensor exhibits an excellent responsiveness when the thickness of the coating 16 is very small, the coating 16 is not highly effective in restricting the mass flow rate and increasing the contact time when the thickness is smaller than 5 μm. When the coating 16 is more than 500 μm thick, the sensor exhibits a poor responsiveness although the output voltage increases, and the coating 16 tends to easily detach from the electrode 14A.

The thickness of the coating 16 can be controlled primarily by the initially performed dry process. The subsequent wet process is not particularly for increasing the thickness of the coating 16 but principally for filling in the relatively large pores of the coating formed by the dry process with fine particles so that the finished coating 16 may have pores of appropriate size and distribution. The relatively fragile matrix resulting from the wet process interlaces with the porous and stout matrix prepared by the dry process and is sustained by the latter matrix. The application of fine particles dispersed in a liquid in the wet process may be carried out in various manners; for example by immersion, spraying, vacuum impregnation or ultrasonic wave impregnation. For applying the fine particles in a sufficiently large quantity to well fill in the large pores, a vacuum impregnation technique is usually most effective and preferable.

The ultimate pore size and total pore volume can be controlled in a wide range by varying the concentration of the dispersion and/or repeating the wet process (impregnation and baking). For example, the wet process will need no repetition when a relatively highly concentrated sol such as 30% silica sol or 10% alumina sol is used, but may be repeated twice when a thinner sol such as 10% silica sol or 5% alumina sol is used.

EXAMPLES

The oxygen sensor of FIG. 1 was produced in the following examples with the coating 16 of various materials and forming procedures. The solid electrolyte 12 was of a stabilized zirconia (85 mol% $ZrO_2$—15 mol% CaO). The tubular electrolyte 12 was initially subjected to ultrasonic wave washing in acetone. A paste containing finely powdered platinum (about 0.1 μm in particle size) was applied onto both sides of the electrolyte 12. Then the electrolyte 12 was fired at 1350° C in air for 1 hr to turn the coated paste into the porous platinum electrode layers 14A and 14B.

The porous coating 16 was formed on the outside of the outer electrode layer 14A generally by the following sequential steps: (1) plasma spraying of preliminarily dried fine particles with a $N_2$-$H_2$ plasma, (2) vacuum impregnation with an aqueous dispersion of fine particles, (3) drying at 150° C in air for 1 hr, and (4) baking at 900° C in air for 1 hr. The first step is called herein the dry process and the steps (2)–(4) are collectively called herein the wet process. The materials for the dry and wet processes were variously combined as shown in Table 2.

Table 2

| Example No. | Materials | |
|---|---|---|
| | Dry process | Wet process |
| 1 | α-alumina (mean particle size: 5 μm) | 5–30% silica sol |
| 2 | same as No. 1 | 5–10% alumina sol |
| 3 | alumina cement (mean particle size: 5 μm) | silica sol |
| 4 | same as No. 3 | alumina sol |
| 5 | spinel (mean particle size: 5 μm) | silica sol |
| 6 | same as No. 5 | alumina sol |
| 7 | α-alumina | aqueous dispersion of γ-alumina (10 Wt%) |
| 8 | same as No. 7 | γ-alumina (10%) dispersed in 10% silica sol (90%) |

The coating 16 was made about 80 μm thick throughout these examples.

The output characteristic of the oxygen sensor produced in Example 1 in the exhaust gas of a gasoline engine was as shown by the curve C in the graph of FIG. 3.

The curve D in the same graph represents the output characteristic of a similar sensor whose coating 16 was formed 80 μm thick by the dry process of Example 1 followed by no wet process. The curve W represents a sensor whose coating 16 (80 μm thick) was formed by applying a dispersion of alumina cement in water glass followed by baking at 900° C in air for 1 hr. The output characteristic of the oxygen sensor according to Example 1 is closest to the theoretical curve. The output characteristics of the sensors produced in Examples 2–8 were almost the same as the curve C.

The graph of FIG. 4 shows the relationship between the contact time of the exhaust gas with the oxegen sensor and the rate of change in the output of the sensor. The curve C represents the sensor produced in Example 7. The curves D and W represent respectively the same sensors as represented by the curves D and W in the graph of FIG. 3. The curves in FIG. 4 show the responsiveness of the respective sensors. The superiority of the sensor of Example 7 is apparent. The sensors of Examples 1–6 and 8 also had substantially the same responsiveness as one represented by the curve C in FIG. 4.

What is claimed is:

1. A method of forming a porous coating on an electrode layer of an oxygen sensor, said sensor comprising a layer of a solid oxygen-ion electrolyte for use in a combustion engine exhaust gas, said layer of said solid electrolyte having first and second sides and having first and second electrode layers formed on said first and second sides respectively; said first electrode layer being in communication with said exhaust gases, said second layer being in communication with a reference gas, said porous coating being formed only on said first electrode layer which is exposed to, and in communication with, said exhaust gases, said method comprising the steps of:

applying fine particles of a heat-resistant and chemically stable first material onto the surface of the electrode layer to form a porous layer by plasma-spraying said fine particles, said first material being selected from the group consisting of alumina, spinel, alumina cement, beryllia, zirconia, nickel oxide, silicon carbide, boron carbide and boron nitride;

applying a dispersion of fine particles of a heat-resistant and chemically stable second material in a liquid onto said porous layer to impregnate said porous layer with said dispersion, said dispersion containing at least one compound selected from the group consisting of alumina and silica; and baking the impregnated porous layer to fix said particles of said second material to said porous coating, said fine particles and said dispersion being applied such that the total pore volume in the porous coating after the completion of the baking step ranges from between about 0.09 to 0.16 $cm^3$ per one gram of the porous coating.

2. The method in accordance with claim 1 wherein the particle size of said fine particles of said first material is in the range of from 5 to 50 $\mu m$.

3. The method in accordance with claim 2 wherein said dispersion is applied to said porous coating by vacuum impregnation.

4. The method in accordance with claim 3 wherein the baking step is carried out at a temperature of about 900° C.

5. The method in accordance with claim 2 wherein said particles of said first material and said dispersion are applied in such quantities that the porous coating has a thickness in the range from 5 to 500 $\mu m$ after the completion of the baking step.

6. A method of forming a porous coating on an electrode layer of an oxygen sensor, said sensor comprising a layer of a solid oxygen-ion electrolyte for use in a combustion engine exhaust gas, said layer of said solid electrolyte having first and second sides and having first and second electrode layers formed on said first and second sides respectively; said first electrode layer being in communication with said exhaust gases, said second layer being in communication with a reference gas, said porous coating being formed only on said first electrode layer which is exposed to, and in communication with, said exhaust gases, said method comprising the steps of:

applying by plasma-spraying fine particles of a heat-resistant and chemically stable first material selected from the group consisting of alumina, spinel, alumina cement, beryllia, zirconia, nickel oxide, silicon carbide, boron carbide and boron nitride onto the outer surface of the electrode layer to form a porous layer, the particle size of said fine particles being in the range from 5 to 50 microns;

impregnating said porous layer with at least one aqueous dispersion system selected from the group consisting of alumina sol, silica sol and an aqueous dispersion of fine particles of alumina; and baking the impregnated porous layer to turn said at least one dispersion system into a solid matrix which consists essentially of at least one of alumina and silica and is intimately fixed to said porous layer, said plasma-spraying of said first material and the impregnation with said at least one dispersion system being performed such that said porous coating has a thickness in the range from 5.0 to 500 microns after the completion of the baking step and that the total pore volume in the porous coating after the completion of the baking step ranges from 0.09 to 0.16 $cm^3$ per one gram of the porous coating.

7. The method in accordance with claim 6 wherein said at least one dispersion system is applied to said porous layer by vacuum impregnation.

8. In an oxygen sensor for detecting a variation in the oxygen concentration in a combustion engine exhaust gas, the sensor having a solid oxygen-ion electrolyte layer, a first electrode layer formed on one side of the electrolyte layer to be exposed to the exhaust gas, a second electrode layer formed on the other side of the electrolyte layer, and a porous coating of a heat-resistant and chemically stable material which comprises at least one of alumina and silica and is formed on the outside of the first electrode layer, the improvement comprising said porous coating consisting of a first porous matrix which is formed by plasma-spraying fine particles of a first material selected from the group consisting of alumina, spinel, alumina cement, beryllia, zirconia, nickel oxide, silicon carbide, boron carbide and boron nitride onto the outer surface of the first electrode layer, the particle size of said fine particles being in the range from 5 to 50 microns, and a second matrix which consists essentially of at least one of alumina and silica and is formed by impregnating said first matrix with at least one aqueous dispersion system selected from the group consisting of alumina sol, silica sol, and an aqueous dispersion of fine particles of alumina and then baking the impregnated first matrix, said porous coating having a thickness in the range from 5 to 500 microns.

9. An oxygen sensor according to claim 8 wherein the total pore volume in said porous coating ranges from between about 0.09 to 0.16 $cm^2$ per one gram of said porous coating.

* * * * *